United States Patent [19]

Sidaway

[11] 4,104,901
[45] Aug. 8, 1978

[54] HARDNESS TESTING MACHINE

[76] Inventor: Joseph Trevor Sidaway, 138 Leavale Rd., Norton, Stourbridge West Midlands, England

[21] Appl. No.: 732,475

[22] Filed: Oct. 14, 1976

[30] Foreign Application Priority Data

Oct. 16, 1975 [GB] United Kingdom ............... 42405/75

[51] Int. Cl.² ............................................. G01N 3/44
[52] U.S. Cl. ............................................ 73/81; 73/83
[58] Field of Search ................................ 73/83, 81, 85

[56] References Cited

U.S. PATENT DOCUMENTS

| 2,188,992 | 2/1940 | Wolpert et al. | 73/81 |
| 2,282,904 | 5/1942 | Tea | 73/81 |
| 2,722,831 | 11/1955 | Smith | 73/81 |
| 2,804,769 | 9/1957 | Clark | 73/81 |
| 3,855,848 | 12/1974 | Sidler | 73/81 |

FOREIGN PATENT DOCUMENTS 445,983  4/1936  United Kingdom ........................ 73/81

Primary Examiner—Anthony V. Ciarlante
Attorney, Agent, or Firm—Merriam, Marshall & Bicknell

[57] ABSTRACT

A hardness testing machine comprises an indenter mounted on one end of a lever. A workpiece clamp is mounted on a further lever to engage the same face of the workpiece as is engaged by the indenter. A piston and cylinder unit is arranged to transfer to the indenter lever a load normally borne by the clamp lever so that load on the workpiece is unchanged. Movement of the indenter arising from the temporary application of the additional load is amplified and applied to a dial gauge.

9 Claims, 7 Drawing Figures

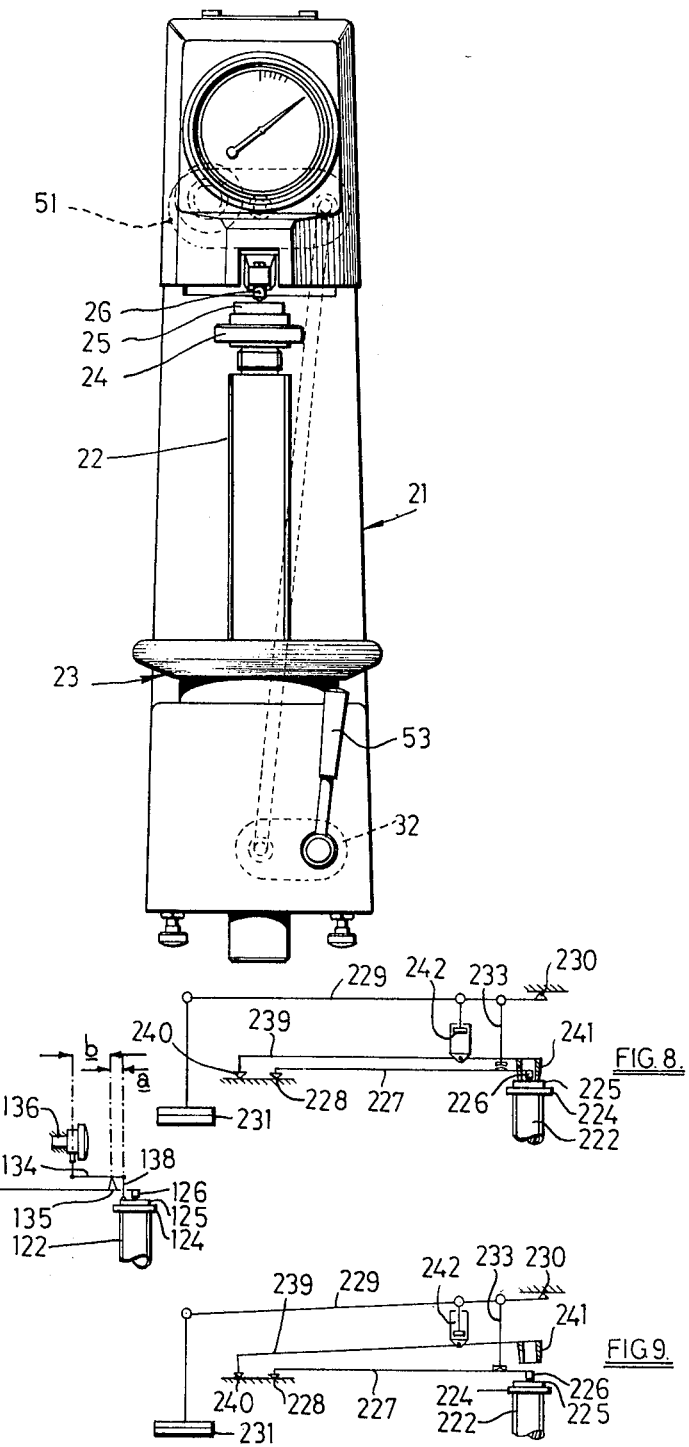

HARDNESS TESTING MACHINE

BACKGROUND OF THE INVENTION

This invention relates to a hardness testing machine of the kind (hereinafter called the kind specified) comprising a support for an object which is to be tested, an indenter which, in use, forms an indentation in the object, and a mechanism for urging the indenter against the object under test.

In known hardness testing machines of the kind specified, the indenter is secured to the lower end of a vertical rod, generally known as the indenter spindle, and the mechanism for urging the indenter against the object under test includes at least one lever connected with the rod at the upper end of the latter. In use, the indenter spindle transmits downwardly directed forces from the lever to the indenter.

In use of a first known type of hardness testing machine of the kind specified, the area of the indentation is determined by measuring a dimension of e.g. the diameter of, the indentation, generally by means of a travelling microscope incorporated in the testing machine.

With a second known type of testing machine of the kind specified, the increase in depth of the indentation which is caused by a predetermined increase in the force which urges the indenter against the object under test is determined. In this second known type of machine, there is connected to the upper end of the indenter spindle a mechanism which transmits movement of the spindle to an indicator and also amplifies this movement so that movement of the indicator which corresponds to a very small movement of the indenter can readily be observed. One source of error in measurements of hardness made with this second known type of machine is vertical movement of the indenter relative to the indenter spindle when under load.

A further source of error, which is more important in connection with the second known type of machine referred to above, but may also be significant in the first known type of machine referred, is the friction which impedes movement of the indenter spindle and friction in the mechanism for urging the indenter against the object under test.

A further disadvantage of known hardness testing machines of the kind specified is that such machines cannot be used, with the indenter mounted directly on the indenter spindle, to test the hardness of internal surfaces of workpieces. To enable the known machines to be used for such measurements, the machines are adapted by the interposition of a goose neck between the indenter spindle and the indenter. Generally, a range of different goose necks is provided with known machines of the kind specified to enable hardness measurements to be made on various surfaces of workpieces of various sizes and shapes. The use of goose necks in machines of the kind specified has a number of disadvantages. The assymetrical shape of a goose neck results in a greater deflection of the machine, when under load, than occurs when the indenter is mounted directly on the spindle. When a goose neck is used, it is difficult to maintain proper alignment of the indenter with the indenter spindle. Large goose necks, which are necessarily heavy, require indenter spindles of special form to enable such goose necks to be properly secured to the spindle. Particularly in the case of heavy goose necks, the mechanism for urging the indenter against the object under test must be adjusted to compensate for the weight of the goose neck which is applied to the indenter. When such adjustments have been made, and the machine is to be used without a goose neck, special weights can be added to the mechanism to compensate for the absence of the goose neck, but this complicates use of the machine. It will also be appreciated that the provision of a variety of goose necks with each machine contributes significantly to the overall cost.

A further disadvantage of the second known type of machine hereinbefore referred to is that an erroneous indication of the increase in depth of the indentation is given in any case where non-elastic collapse of the object being tested occurs at that face of the object which engages the support, i.e. the face remote from the indenter. Such non-elastic collapse is likely to occur in cases where the surface of the object under test which is engaged with the support is not a machined surface, for example a surface formed by casting or forging.

A still further disadvantage of known machines of the kind specified, both when used with a goose neck and when the indenter is attached directly to the spindle, is that visibility of the surface area of the object at which the hardness is to be tested is restricted.

SUMMARY OF THE INVENTION

It is an object of the present invention to provide a hardness testing machine of the kind specified which reduces or overcomes one or more of the foregoing disadvantages.

According to the present invention, there is provided a hardness testing machine of the kind specified in which the indenter is mounted on a lever, called herein the indenter lever.

Tests of hardness of internal surfaces of objects and of other surfaces, the accessibility of which is poor, can be made more conveniently with a machine in accordance with the invention, than with known machines of the kind specified.

The indenter lever preferably has a fulcrum adjacent to one end and the indenter is preferably mounted adjacent to the opposite end of the indenter lever.

BRIEF DESCRIPTION OF THE DRAWINGS

The invention will now be described by way of example with reference to the accompanying drawings wherein:

FIG. 4 shows an elevation of a front end of the machine in FIG. 3, FIG. 7 is a diagrammatic illustration of a modification of the machine of FIG. 3, FIG. 8 is a diagrammatic illustration of a further modification of the machine of FIG. 3, the machine being illustrated prepared for use, and FIG. 9 is a diagram similar to FIG. 8 illustrating the parts during formation of an indentation.

DETAILED DESCRIPTION

Figure 1:
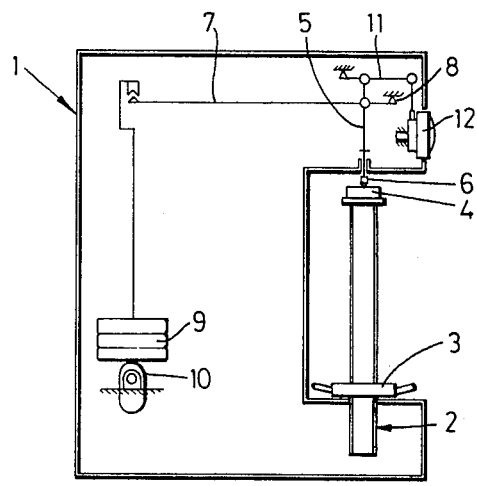
FIG. 1 is a diagrammatic illustration of a known hardness testing machine of the kind specified incorporating an indenter spindle.

The machine illustrated in FIG. 1 comprises a frame 1 which carries a vertical lead screw 2 which can be raised and lowered by a manually-rotatable nut 3. The screw is adapted to support at its upper end a workpiece 4, a surface of which is to be subjected to hardness testing. The machine further includes an indenter spindle 5 which is co-axial with the screw 2, is situated above the screw and is guided for movement towards and away from the screw. To the lower end of the spindle 5 there is attached an indenter 6 having a pointed lower end for engagement with the workpiece 4.

The machine of FIG. 1 further comprises a mechanism for urging the indenter 6 against the workpiece 4. This mechanism comprises a first lever 7 having at one end a fulcrum 8 on the machine frame 1. At a position spaced somewhat along the lever from the fulcrum, the lever is coupled to the indenter spindle 5. The mechanism further comprises a set of weights 9, so arranged that they can be suspended from that end of the lever 7 which is opposite to the fulcrum 8. Normally, as shown in FIG. 1, the weights 9 are supported by a cam 10.

The machine of FIG. 1 further comprises indicating means for indicating the magnitude of vertical movements of the spindle 5 and indenter 6. This indicating means comprises a further lever 11 which has at one end a fulcrum on the machine frame 1. At its opposite end, the lever is coupled with a dial gauge 12 which provides a visual indication of movements of the spindle 5. The lever 11 is coupled at a position between its ends with the upper end of the spindle 5, the lever being so arranged that vertical movements of the spindle are amplified and applied to the dial gauge 12.

In order to measure the hardness of the workpiece 4 by means of the machine shown in FIG. 1, the lead screw 2 is adjusted until the indenter 6 is in contact with the workpiece and the dial gauge 12 indicates zero depth. The indenter then bears a preliminary load which includes the weight of the spindle 5, the weight of the lever 7 and any further weights which may be applied to establish the required preliminary load. The cam 10 is then turned to apply the weights 9 to the lever 7, thereby applying an additional load to the indenter 6. When it can be seen from the dial gauge 12 that the indenter spindle has come to rest, the cam 10 is returned to its original position to remove the additional load. The increase in depth of the indentation caused by the temporary imposition of the additional load onto the preliminary load is then ascertained from the reading of the dial gauge 12.

Figure 2:
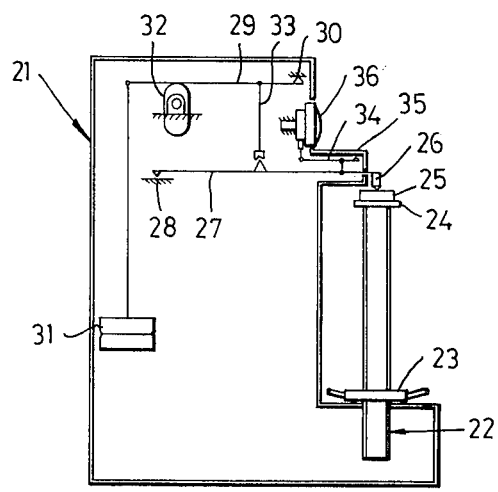
FIG. 2 is a similar diagrammatic illustration of a machine in accordance with the present invention.
Figure 3:
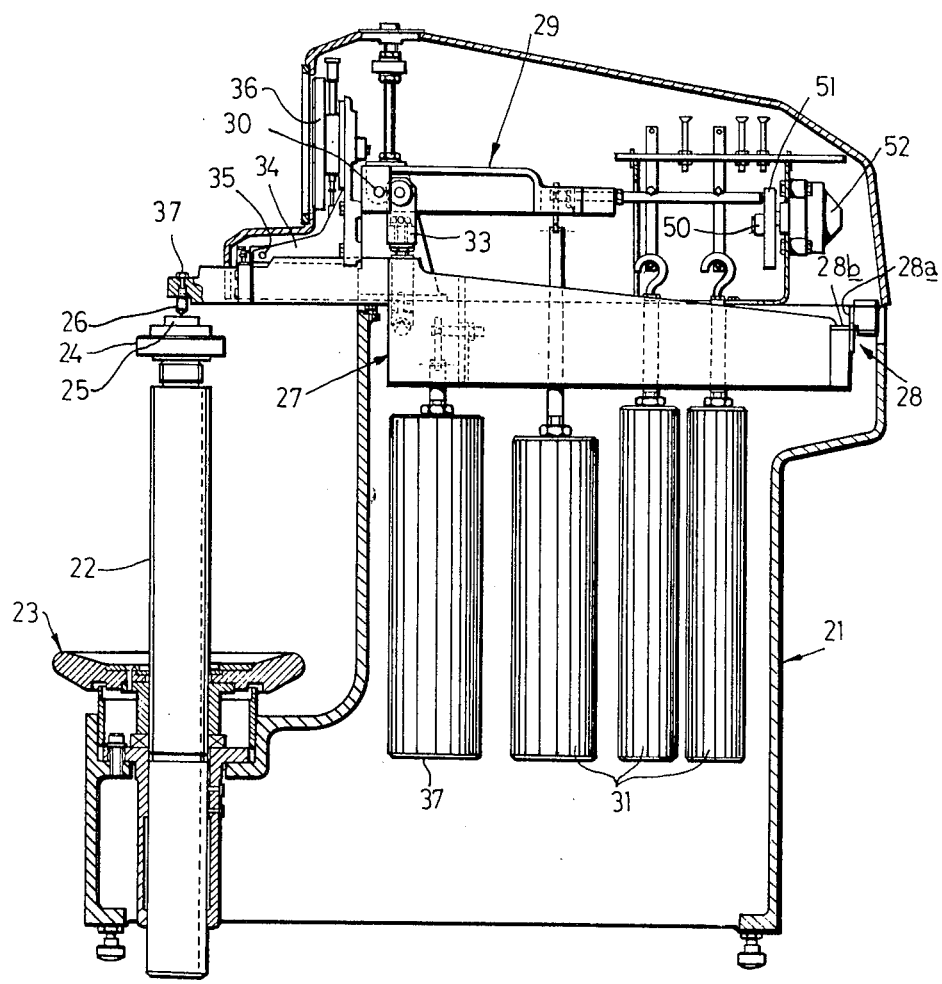
FIG. 3 shows a cross-section of a specific machine arranged generally as shown in FIG. 2.

The machine illustrated in FIGS. 2 to 4 has a frame 21 carrying a vertical lead screw 22 which is adjustable relative to the frame by a nut 23. On the upper end of the lead screw there is provided a support 24 for a workpiece 25 under test. These parts may be similar to the corresponding parts of the known machine illustrated in FIG. 1. The machine of FIGS. 2 to 4 also has an indenter 26 which may be similar to known indenters.

In the machine of FIGS. 2 to 4, the indenter 26 is mounted on a lever 27 at one end thereof. At its opposite end, the lever has a fulcrum 28 on the machine frame 21. In a case where the indenter is intended to be urged vertically downwardly onto the workpiece 25, the lever 27 is substantially horizontal, so that when the lever moves about the fulcrum 28 the indenter 26 will move along an arc of a circle which approximates very closely to a vertical path. It will be appreciated that the distance through which the indenter moves when the machine is in use is very small indeed, as compared with the length of the lever 27.

The fulcrum 28 is provided by four flexible strips of spring steel. Two only of these, 28a and 28b, are shown in FIG. 3. Typically, each strip has a thickness of 28 thousandths of an inch, a length of 1½ inches and a width of ⅜ inch. The strip 28a is arranged vertically with its largest faces presented forwardly and rearwardly of the machine. Slightly less than a lower half of the strip overlaps with a rearwardly presented face of the lever 27 and this lower portion of the strip is rigidly secured to the lever. Slightly less than an upper half of the strip overlaps with a forwardly presented face on the machine frame 21. This upper portion of the strip is rigidly secured to the frame. The strip 28a is situated adjacent to one lateral extremity of the lever 27. A further one of the strips is similarly arranged adjacent to the opposite lateral extremity of the lever and is typically spaced from the strip 28a by a distance in the region of 2 inches. The strip 28b is arranged horizontally with its length extending from front to rear of the machine. Slightly less than the front half of the strip 28b overlaps an upwardly presented face of the lever 27 and this front portion of the strip is rigidly secured to the lever. Slightly less than the rear half of the strip 28b overlaps with a downwardly presented face on the frame 21 and this rear portion of the strip is rigidly secured to the frane. The fourth strip is similarly arranged, the horizontal strips being disposed between the vertical strips. The flexible strips collectively provide for pivoting movement of the lever 27 relative to the frame about a horizontal axis which extends from side to side of the machine. It will be understood that the fulcrum 28 does not give rise to any frictional forces which oppose such pivoting of the lever 27.

The machine of FIGS. 2 to 4 further includes a mechanism for urging the indenter 26 against the workpiece 25. This mechanism includes a second lever 29 having at one end a fulcrum 30 on the machine frame 21. On a part of the lever 29 remote from its fulcrum there is suspended a set of weights 31. The mechanism further includes a rod 33 which is coupled to the lever 29 at a position between its ends but nearer to the fulcrum 30 than to the opposite end. The rod 33 is adapted to transmit downwardly directed force from the lever 29 to the lever 27 at a position between the indenter 26 and the fulcrum 28.

A roller 50 is provided for supporting the lever 29, in order to relieve the indenter 26 of the load derived from the weights 31. In FIG. 3, the roller 50 is shown spaced from the lever 29 so that the additional load is applied to the indenter. The roller 50 is carried on a lever 51 which can pivot about a horizontal axis to move the roller from the position shown in FIG. 3 into engagement with the underside of an end portion of the lever 29 remote from the fulcrum 30. Movement of the lever 51 is controlled by a dash pot 52 which limits the rate at which the additional load can be applied to the indenter.

A handle 53 is provided at the front of the machine to enable an operator to turn a cam or crank 32 from which motion is transmitted to the lever 51 to move the roller 50 into and out of engagement with the lever 29.

The machine further comprises indicating means for indicating vertical movement of the indenter 26. This indicating means comprises a third lever 34 which has near to one end a fulcrum 35 on the machine frame 21. The opposite end of the lever 34 is coupled to a dial gauge 36. At the end adjacent to the fulcrum 35 the lever 34 is coupled to the lever 27 at a position between the ends of the latter. The lever 34 is arranged to amplify movement of the lever 27 and to apply such amplified movement to the dial gauge 36.

The machine illustrated in FIGS. 2 to 4 is used in a similar manner to that already described with reference to the machine of FIG. 1. Initially, the weights 31 are supported by the roller 50 and the indenter 26 is urged downwardly by a preliminary load which includes the weight of the lever 27 and of a further weight 37. When the cam 32 is turned, the indenter is subjected to an additional downward load derived from the weights 31. When the downward movement of the indenter has ceased, the cam 32 is returned to its initial position and the increase in depth of the identation in the workpiece 25 caused by the temporary additional load is ascertained from the dial gauge 36.

It will be appreciated that a hollow cylindrical workpiece can readily be supported on the support 24 with the indenter 26 in contact with an internal surface of the workpiece.

As shown in FIGS. 3 and 4, the indenter 26 is disposed at the underside of the lever 27 and is secured to the lever by means of a screw 37. This screw draws the indenter against the underside of the lever and establishes between the lever and indenter a contact pressure which is at least equal to the maximum contact pressure which would be established when both the preliminary load and the additional load are transmitted from the lever to the indenter. This arrangement ensures that there is no vertical movement of the indenter relative to the lever under load.

Figure 5:
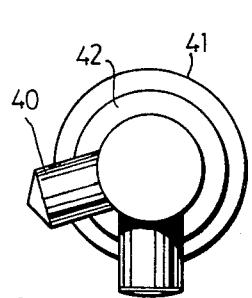
FIG. 5 is an end view of an indenter arm of a further machine arranged generally as shown in FIG. 2.
Figure 6:
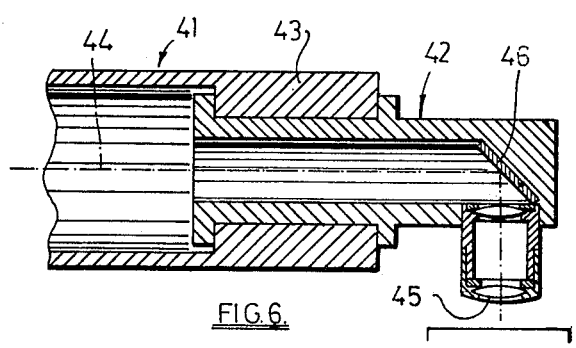
FIG. 6 shows a cross-section of the arm of FIG. 5.

In FIGS. 5 and 6 there is illustrated the indenter 40 and an adjacent end portion of a lever 41 of a further machine arranged generally as shown in FIG. 2. The lever 41 corresponds to the lever 27 of FIG. 2. The lever 41 includes a turret 42 which is mounted on a further portion 42 of the lever for rotation about a longitudinal axis 44 of the lever. The indenter 40 is secured to the turret 42 and projects therefrom radially with respect to the axis 44. Also mounted on the turret 42 are certain components of an optical system of the machine. These components include an objective lens 45 which is spaced from the indenter 40 angularly about the axis 44. By turning the turret about the axis, a selected one of the indenter 40 and objective lens 45 can be directed towards a test area of the workpiece. The lever 41, including the turret 42, is hollow and light which passes through the objective lens is reflected by a reflecting mirror or prism 46 through the lever to further components (not shown) of the optical system of the machine. This optical system is arranged in a known manner to enable the diameter or another dimension of an indentation formed in the workpiece to be determined.

In FIG. 7 there is shown a means for measuring the depth of the indentation which is an alternative to the means shown in FIGS. 2 to 4. Parts shown in FIG. 7 which correspond to parts already described with reference to FIGS. 2 to 4 are indicated by like reference numerals with the prefix 1 and the preceding described is deemed to apply, except for the differences hereinafter mentioned.

In the apparatus illustrated in FIG. 7, the fulcrum 135 of the amplifying lever 134 is on the main indenter lever 127 at a position similar to that of the fulcrum 35. One end of the lever 134 is connected to the dial gauge 136 but the other end of the lever 134 is free to move relative to the frame 21 and carries a probe 138 which contacts the surface of the workpiece 125 under test.

If, when subjected to a load by the indenter 126, the upper surface of the workpiece 125 remains stationery relative to the machine frame, i.e. there is no collapse of the under surface of the workpiece, operation will be the same as that of the machine of FIGS. 2 to 5 and the gauge 136 will indicate only movement of the indenter due to indentation. If, during the indentation, there is downward movement of the upper surface of the workpiece 125 relative to the machine frame, there will be a corresponding downward movement of the probe 138.

Downward movement of the probe 138 causes rocking of the lever 134 in a direction opposite to that of rocking movement of the lever caused by downward movement of the indenter 126. Movement of the probe will tend to compensate for excessive downward movement of the indenter which results from collapse of the workpiece under test at its under surface. This compensation will not be exact, as the amplification of movement of the probe 138 differs from that of movement of the indenter 126. However, the compensation will be sufficient for practical purposes if the fulcrum 135 is sufficiently close to the probe 138. Referring to FIG. 8, if the distance from the probe to the fulcrum 135 is $a$ and the distance from the fulcrum to the other end of the lever 134 is $b$, then the amplification of movement of the lever 127 will be $(b + a)/a$ and the amplification of movement of the probe 138 will be $b/a$. The difference is $[(b + a)/a] - (b/a) = 1$.

In FIGS. 8 and 9, there is illustrated a further modification of the apparatus shown in FIGS. 2 to 5. For the sake of clarity, the depth-measuring means is not shown in FIGS. 8 and 9. Parts shown in FIGS. 8 and 9 which correspond to parts already described with reference to FIGS. 2 to 5 are indicated by like reference numbers with the prefix 2 and the preceding description is deemed to apply, except for the differences hereinafter mentioned.

As compared with the apparatus of FIGS. 2 to 4, the apparatus illustrated in FIGS. 8 and 9 comprises a further lever 239, called herein a clamping lever. At one of its ends, the lever 239 has a fulcrum 240 on the machine frame. On the other end of the lever there is a clamp 241 for engaging the workpiece 225. The arrangement is such that the clamp can exert on the workpiece a force which can be considered as acting at the point of contact between the indentor 226 and the workpiece and being directed along the path of movement of the indenter. The clamping lever is connected with the additional load lever 229 by an hydraulic piston and cylinder unit 242.

When the apparatus of FIGS. 8 and 9 is prepared for use, the indenter 226 is applied to the workpiece 225 with the preliminary load. The piston and cylinder unit 242 is extended so that the load derived from the weights 231 is imposed on the clamping lever 239, not on the indenter lever 227. The workpiece 225 is thus urged against its support 224 by the clamp 241. The mechanical arrangement is such that the force exerted on the workpiece by the clamp is equal to the additional load subsequently applied to the indenter 226 to increase the depth of the indentation in the workpiece.

To apply the additional load to the indenter 226, the piston and cylinder unit 242 is contracted. The clamp 241 is thereby relieved of the load derived from the weights 231. It will be noted that application of the additional load to the indenter is not accompanied by any increase in the pressure exerted by the workpiece on the support 224, or by any increase in the load to which the support 224, the lead screw 222 and the machine frame are subjected. Accordingly, errors resulting from deformation of these parts or collapse of the under face of the workpiece under the additional load can be avoided. The additional load is removed from the indenter by extending the piston and cylinder unit 242 once more, thereby applying an equal load to the workpiece via the clamp 241.

I claim:

1. In a hardness testing machine having a support for an object which is to be tested, an indenter which, in use, forms an indentation in the object, an indenter lever on which the indenter is mounted and a mechanism for urging the indenter against the object under test, the improvement wherein the indenter lever is arranged for applying a preliminary load to the indenter to urge same against the object, said mechanism includes means for exerting an additional load on the indenter and the machine further comprises a clamp for applying a load substantially equal to the additional load to an object on the support prior to application of the additional load to the indenter, and means operative for transferring said applied additional load from said clamp to said indenter and thereby applying the additional load by the indenter to the object and relieving the object of the load applied thereto by the clamp.

2. The improvement according to claim 1 comprising means for transferring the additional load from the clamp to the indenter.

3. The improvement according to claim 1 wherein the clamp is carried on a clamping lever and said means for transferring the additional load comprises a piston and cylinder unit connected between the clamping lever and a member through which the additional load is transmitted to the indenter.

4. The improvement according to claim 1 comprising an indicator for indicating the magnitude of a movement of the indenter lever about its fulcrum, an amplifying lever coupled to said indenter lever and coupled also to the indicator, the amplifying lever being arranged to amplify the movement of the indenter lever and to apply such amplified movement to the indicator and the amplifying lever having a probe arranged for engagement with that surface of an object on the support which is also engaged by the indenter, whereby movement of said surface is transmitted to the amplifying lever.

5. The improvement according to claim 4 wherein the amplifying lever is coupled to the indenter lever at a position between the indenter and the fulcrum of the indenter lever.

6. The improvement according to claim 1 comprising a screw which draws the indenter against the indenter lever and establishes between the indenter and the lever a contact pressure sufficiently large to avoid significant movement of the indenter relative to the lever when the machine is used.

7. In a hardness testing machine having a support for an object which is to be tested, an indenter which, in use, forms an indentation in the object, an indenter lever on which the indenter is mounted, the lever being pivotally supported about a fulcrum and said indenter being fastened adjacent an end of the lever, a mechanism for urging the indenter against the object under test, means for applying a preliminary load to the indenter lever to urge the indenter against the object, said mechanism including means for exerting an additional load on the indenter lever, an indicator for indicating the magnitude of a movement of the indenter when said additional load is exerted on said indenter lever, and means connected between said indicator and a point on said indenter lever, said point being located between said fulcrum and said indenter and at a distance from said indenter 8. The improvement according to claim 7 wherein the indicator is spaced from the indenter in a direction along the indenter lever towards the fulcrum of the indenter lever and said means for transmitting motion to the indicator is coupled to the indenter lever at a position thereon between the indenter and said fulcrum.

9. In a hardness testing machine having a support for an object which is to be tested, an indenter which, in use, forms an indentation in the object, a mechanism for urging the indenter against the object under test and an indicator for indicating the magnitude of a movement of the indenter, the improvement wherein the machine includes an indenter lever on which the indenter is mounted for movement about a fulcrum of the indenter lever and means for transmitting to the indicator motion of the indenter lever at a position spaced longitudinally of the indenter lever from the indenter, said means for transmitting motion to the indicator comprising a further lever coupled to said indenter lever and coupled also to the indicator, said further lever having a probe arranged for engagement with that surface of an object on the support which is also engaged by the indenter, whereby movement of said surface is transmitted to said further lever.

* * * * *